United States Patent [19]

Bennett

[11] 4,368,983

[45] Jan. 18, 1983

[54] ABSOLUTE REFLECTOMETER

[75] Inventor: Harold E. Bennett, Ridgecrest, Calif.

[73] Assignee: The United States of America as represented by the Secretary of the Navy, Washington, D.C.

[21] Appl. No.: 206,331

[22] Filed: Nov. 13, 1980

[51] Int. Cl.³ ............................................. G01N 21/55
[52] U.S. Cl. ................................................... 356/445
[58] Field of Search ................................ 356/445–448, 356/369, 237; 250/571, 572, 559, 562

[56] References Cited

U.S. PATENT DOCUMENTS

| 3,160,752 | 12/1964 | Bennett | 250/83.3 |
| 3,402,634 | 9/1968 | Bennett | 88/14 |
| 3,421,079 | 1/1969 | Bennett et al. | 324/61 |
| 3,499,716 | 3/1970 | Bennett | 356/209 |
| 3,771,880 | 11/1973 | Bennett | 356/209 |
| 3,947,127 | 3/1976 | Bennett et al. | 356/124 |

OTHER PUBLICATIONS

Versatile High–Precision Multiple–Pass Reflectometer by O. Arnon and P. Baumeister, Applied Optics, vol. 17, No. 18, Sep. 15, 1978.
Scattering Characteristics of Optical Materials by H. E. Bennett, vol. 17, No. 5, Optical Engineering, Sep.–Oct. 1978.

Primary Examiner—Bruce Y. Arnold
Attorney, Agent, or Firm—Robert F. Beers; W. Thom Skeer; Kenneth G. Pritchard

[57] ABSTRACT

An apparatus and method to measure the absolute reflectivity of a sample is made by use of a multiple pass reflectometer. A given light beam permits measurement of the absolute reflectivity by comparing a portion of the light beam in a reference White cell to the change in light of another portion of the beam which undergoes equivalent reflections except for the addition of the sample in one configuration as compared to the other.

8 Claims, 7 Drawing Figures

ABSOLUTE REFLECTOMETER

BACKGROUND OF THE INVENTION

1. Field of the Invention

The present invention is for measuring specular reflectance from a given sample. In particular, it pertains to making absolute measurements with the reflectometer by the use of multiple pass reflections off of the sample. This permits high reflectivity samples to be accurately measured by repeating the number of reflections off the sample a known number of times.

2. Description of the Prior Art

U.S. Pat. No. 3,499,716 to Harold E. Bennett disclosed how to make specular reflections at nearly normal incidence. As was disclosed in the Bennett patent an absolute reflectometer can be made by a variation of a Strong absolute reflectometer as shown in FIG. 1. The strong reflectometer used a flat mirror for mirror 25 whereas the Bennett double reflection technique used a spherical mirror for mirror 25 of FIG. 1 and spherical mirrors 21 and 23 to reflect light off of sample S. The advantage of using spherical mirrors is that a slight sample tilt, as shown by a shift of sample S to position S', permits the deflected light beam to be reimaged to the same position. The use of a spherical mirror 25, having its center of curvature on the sample surface, results in the measurement being insensitive to sample tilt. A plane sample is shown in FIG. 1 and the center of curvature of mirror 25 is halfway between the location of the two beams striking the surface of sample S on the surface of sample S. Tilting the sample causes the light to follow the dotted lines and strike mirror 25 at a different location. However, since a spherical mirror used at its center of curvature returns light to the same point regardless of where it strikes the spherical mirror surface, on second reflection from the flat sample S, the error and tilt is exactly cancelled and the light leaves along the same path whether the sample is tilted or not.

FIG. 2 is a complete light ray path of the Bennett double reflection absolute reflectometer. Mirrors 22, 24, 26, 28, 30, 32, 34, 36, 38, 42, 44, and 46, are plane mirrors. Mirrors 19, 21, 23, 25, 27, 29, 31, 33, and 35 are spherical mirrors. For a detailed breakdown of how the prior Bennett reflectometer functions with regard to FIG. 2, the reader is referred to U.S. Pat. No. 3,499,716 which is herein incorporated by reference. In general, FIG. 2 can be described as comparing measurements with and without sample S for two different configurations. The first is with S as shown and with light reflected to detector D. Next, sample S is removed and the reflection path which is followed for mirrors 30 to 23 to S to 25 to S to 21 to 32 is now altered to have reflection along the path from 30 to 23 to 33 to 21 to 32. While equal path lengths are involved, it is noticed that for comparison purposes that mirrors 33 and 25 have to be either identical or interchangeable. If the sample is rotated 180° and mirrors 30 and 32 are interchanged, the following two measurements occur. Light first follows the dotted path for mirror 32 to 31 to S to 33 to S to 29 to 30 and with the sample removed light travels from 32 to 31 to 25 to 29 to 32. If mirrors 25 and 33 are identical, the ratio of the measurements with the sample in the light path to out of the light path gives the square of the sample reflectance directly. If mirrors 25 and 33 are not identical, they may be effectively interchanged by rotating the sample with mirrors 30 and 32 and measurements taken to obtain a second ratio. If the product of the two ratios is taken, it will give the fourth power of the absolute reflectance and the contribution from the non-identical mirrors cancels. The measurement statistics also improve since twice as many measurements are made as for a single configuration. As described previously, the system is insensitive to sample tilt, the most common source of error in reflectance measurements. The quoted accuracy for the system is ±0.1%.

A systematic error will arise in the double reflection system of FIG. 2 if the center of curvature of the spherical mirror is not accurately in the sample surface. The requirement for exact positioning is, from diffraction theory, that the center of curvature not be displaced from the sample surface by more than half the focal range of the mirror. The focal range F is given by $F = 4\lambda f^2$ where f is the f number of the mirror, the ratio of focal length to the effective diameter of the sample opening for a parallel beam of incident light. $\lambda$ represents the illuminating wavelength of light. For a f/1 system, the requirement is that the center of the mirror coincide with the sample surface to within two wavelengths of light, a difficult requirement. The restrictions ease rapidly as the f number increases.

A simpler, prior art, form of absolute reflectometer is shown in FIG. 3. The reflectometer employs a single sample reflection and a movable detector 50 which swings about an axis 52 through the sample surface to pick up the "sample-in" and "sample-out" beams. The ratio of the two signals then determines the reflectance directly. The disadvantage of this system is that in addition to the requirement for accurately positioning the detector, the reflected beam is reversed left for right on the detector compared to the "straight through" position. Detector non-uniformities significantly limit the accuracy possible using a single reflectance absolute system. If the reflectance of a standard is known accurately, and the position of the sample and standard can be accurately adjusted to coincide, for example, by autocorrelation, the single reflectance technique can give reflectance values with high precision.

An alternate approach for measuring mirror reflectance with precision is to employ a White cell. White cell principles are shown in FIG. 4 for a folded White cell. FIG. 4 shows the principle of the White cell and its folded configuration. Mirrors $M_1$ and $M_3$ both have their centers of curvature on the surface of $M_2$, whose center of curvature is centered between their surfaces. Incoming light is focused at point 0. It is reflected by the sample mirror $M_S$ to $M_1$ at point 1. The dotted lines represent reflect angular dispersion of the light ray. Mirror $M_1$ reimages point 0 on the surface of $M_2$ at point 2. $M_2$ in turn reflects this light to $M_3$ at point 3 which reimages the focus again on the surface of $M_2$ at point 4. Reflection continues to point 5 and point 6 in a similar manner. Reflected light then goes to $M_3$ at point 7 where it is reimaged at point 8 and falls on a detector. By adjusting the tilt of $M_1$ and $M_3$, any odd number of reflections from $M_2$ can be obtained. For highly reflecting mirrors, hundreds of passes between mirrors are possible. White cells were invented to produce very long path lengths in a gas filling the cell without exceeding the dimensions of the laboratory. They are also useful for obtaining multiple reflections on mirrors without losing light. The key to the performance of the White cell is mirror $M_2$, which reimages the surfaces of $M_1$ and $M_3$, so that none of the light specularly reflected from these mirrors is lost. It thus plays a role similar to that played by mirror 25 in the double bounce reflectometer shown in FIGS. 1 and 2.

Let $N=1,3,5\ldots$ the number of reflections on $M_2$. Then the number of reflections for mirrors $M_1$, $M_2$, and $M_3$ are 3, 7, 11 ... $2N+1$. There are initially three reflections and they increase by four every time thereafter. The ratio of the flux I emerging from the White cell to that entering it, $I_O$, is $$I/I_O = R_1^{(N+1)/2} R_2^N R_3^{(N+1)/2} R_s^{(2N+2)}$$

If we take an average value R for mirrors $M_1$, $M_2$, and $M_3$ and define it by $$R^4 = R_1 R_2^2 R_3,$$

the equation for $I/I_O$ can be written $$I/I_O = R_s^{2N+2} R^{2N+1} \quad N=1,3,5\ldots,$$

where $R_s$ = the reflectivity of the sample mirror and $R_1$, $R_2$, and $R_3$ represent the reflectivity of mirrors $M_1$, $M_2$, and $M_3$ respectively.

SUMMARY OF THE INVENTION

The multiple pass absolute reflectometer is made by having a reference light beam divided by a beam splitter. The two subsequent beams leaving the beam splitter are measured relative to one another. One beam in the splitter has passed through a reference White cell and is measured by a detector. The other beam from the beam splitter is subjected to multiple passes off of the sample and then measured by a detector. The detectors determine a relative comparison level between the two beams. The beam that has been multiply reflected off of the sample now undergoes the same number of reflections off of supporting mirrors except that the mirror orientation has now rotated such that with the sample removed the identical path length remains, only the reflections from the sample are omitted. Once again the reference level between the two detectors can be compared. The difference in reference levels between the detectors for the sample-in and sample-out configuration provides an absolute measure of the total light lost for the number of reflections off the sample.

By changing the relative location of supporting mirrors, two possible configurations for multiple pass measurements on a sample can be made. One configuration has a reference mirror with a spherical surface whose center of curvature is located on the sample surface. The second configuration matches the three mirror arrangement of a White cell and has the spherical mirrors reflecting off of a sample such that the center of curvature for the spherical mirror $M_2$ is located between the two reference mirrors $M_1$ and $M_3$ of the standard White cell.

DESCRIPTION OF THE PREFERRED EMBODIMENT

Figure 5:
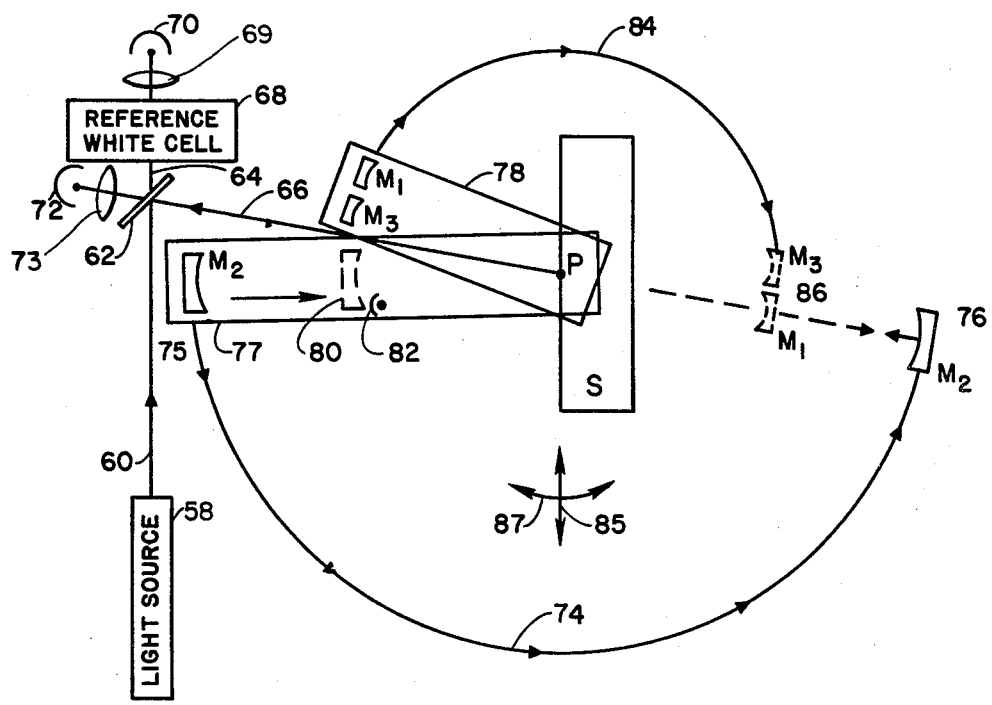
FIG. 5 is a diagram of the present invention.

FIG. 5 shows a view of the present invention. Reference light beam 60 from a light source 58 travels as indicated. The light strikes a beam splitter 62 and is divided into two paths 64 and 66. Path 64 passes through a reference White cell 68, a focusing optic 69, and the output is measured by detector 70. The path length of light through reference White cell 68 is identical to the path in air travelled by beam 66 prior to reaching detector 72. Light reflected off of beam splitter 62 along path 66 strikes sample S at point P and is reflected at near normal incidence to mirror $M_2$. $M_2$ is a spherical mirror which reimages light back on sample S at point P and back along path 66 through beam splitter 62 to detector 72. To do this, mirror $M_2$ is not only spherical but has its center of curvature on the surface of S so that $M_2$ reimages light on the same spot on S for a second reflection. On a second reflection from S, wavefront aberrations introduced in the first reflection are largely cancelled. This system is therefore insensitive to any power in S and is useful for measuring spherical, cylindrical, or aspheric as well as flat samples. The light should be focused to a small spot on the sample surface since light striking the right side of the spot initially will be reimaged on the left side by mirror $M_2$ so that cancellation of the figure induced changes in the wavefront is not complete unless the sample is a flat.

To calibrate the reflectometer in the double reflection configuration just described, mirror $M_2$ is swung around as shown by arc 74 and sample S is removed. In new position 76, $M_2$ is at the virtual image position of $M_2$ formed by S as viewed at detector 72 through focusing optic 73. The total path length from beam splitter 62 to mirror $M_2$ is identical for the two configurations. Light travelling along beam 66 reflects off of mirror $M_2$ once for each configuration. Thus, the only difference in light is the fact that in the first configuration shown light reflects twice off of the sample. By comparing the relative intensity of light in detectors 70 and 72 for each configuration, the difference in light lost when mirror $M_2$ is in position 75 is due to two reflections off of the sample.

By mounting $M_2$ on a slide on a rotatable bar with pivot point P on the surface of S, reflectance measurements at non-normal incidence may also be made. Arrows 85 and 87 show directions sample S can be moved through. Mirror $M_2$ can then be moved about the arc shown to determine reflectance as a function of angle of incidence. For simplicity, S is assumed to rotate about an axis in the plane of the sample passing through P and normal to the drawing. It is also assumed to rotate about an axis normal to its surface and to translate along its surface so that the entire surface of the mirror can be scanned. For a large mirror, only the rotation normal to the mirror surface is performed by the sample mirror. The other motions are achieved by pivoting the input beam about point P and by moving P laterally rather than moving S.

Figure 1:
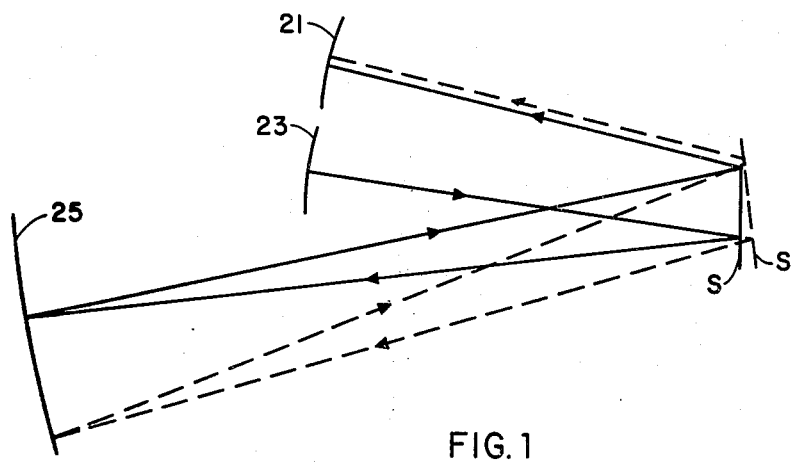
FIG. 1 is a prior art ray path for correcting for sample slip.
Figure 2:
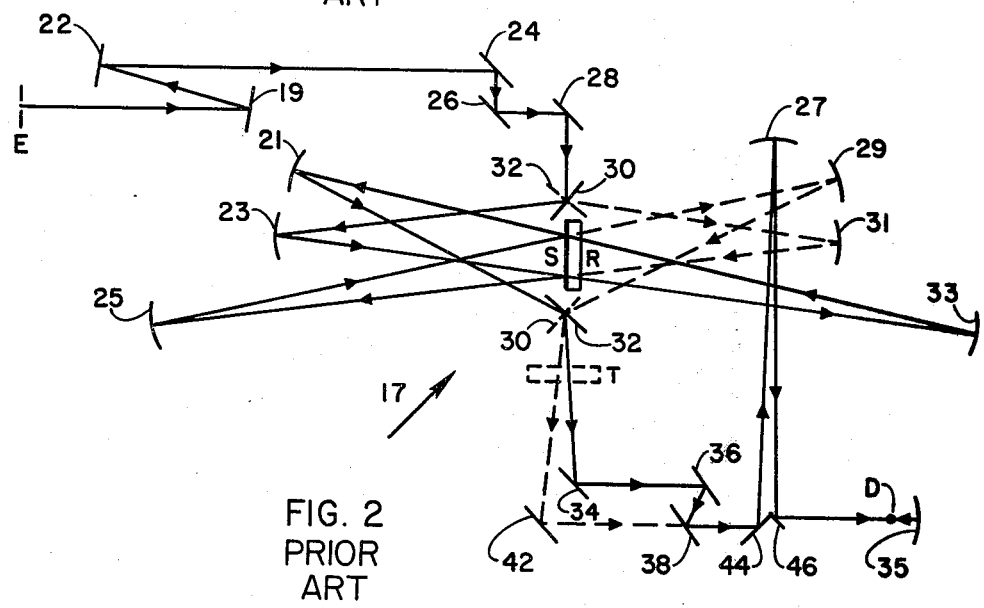
FIG. 2 is a prior art absolute reflectometer.
Figure 3:
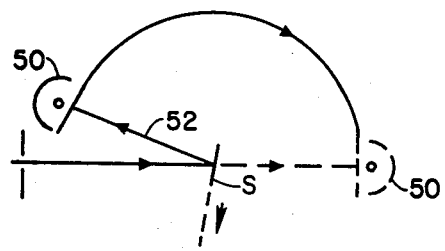
FIG. 3 is a ray path for a single reflection absolute reflectometer.
Figure 4:
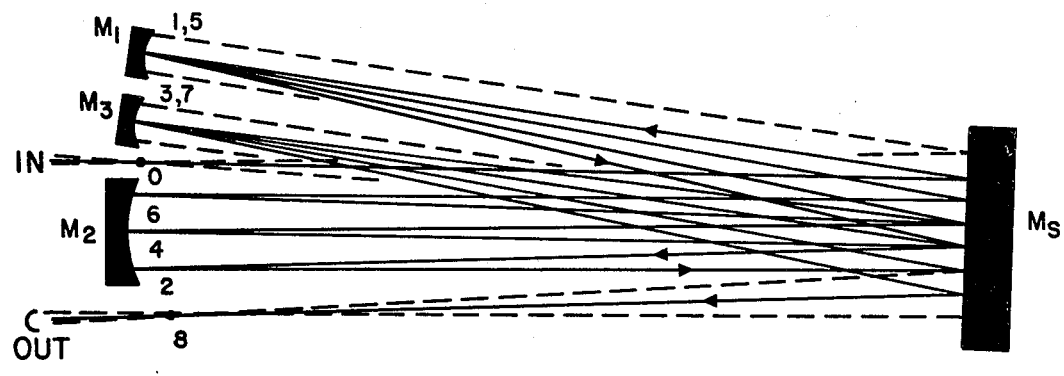
FIG. 4 is a ray path for a folded White cell.

For high reflectivity samples, a double pass reflectometer is insufficient. In modern laser devices, very high reflectivity of mirror surfaces is required. In reflectometers made previously, the number of reflections off the sample are insufficient to lower the amount of signal strength to an easily measured level. The White cell can be folded as shown in FIG. 4 to become a multiple pass absolute reflectometer. While the original purpose of the White cell was to increase path length, the folded White cell permits multiple reflections by inserting the folding mirror $M_s$ and moving $M_1$ and $M_3$ to intercept the reflected light. Refer back to FIG. 4 and the equation $$I/I_O = R_s^{2N+2} R^{2N+1} \quad N=1,3,5\ldots$$

Mirrors $M_1$ and $M_3$ can be rotated about an axis P, which lies in the plane of the sample, until they coincide with their virtual images formed by $M_s$. By removing $M_s$, the value $I'/I = R^{2N+1}$ is obtained. The White cell concept is used to develop an absolute reflectometer which gives powers of the reflectance of the sample to be measured. To a good approximation, the drop in signal from a high reflectance mirror which suffers X reflections is X times that for a single reflection. If $N=5$, for example, $X=12$ and for equal signal to noise ratios and linearity in the detectional electronics, the precision of measurement which is obtainable from a White cell type reflectometer should be better than that for a single bounce system by over an order of magnitude. N values as high as 100 have been obtained in the laboratory for White cell work. To take a numerical example, if the sample has a reflectance of 0.998 and eight reflections are used, the ratio would be 0.984. If 32 reflections are used, the ratio is 0.938. If the precision with which the ratio could be measured were $\pm 0.002$, a value which has been exceeded by a factor of four in some present systems, the statistical uncertainty in reflectance of the sample when 32 reflections are used is $\pm 6 \times 10^{-5}$. If systematic errors are eliminated, this system provides reflectance values for laser mirror reflectors which are 1 to 2 orders of magnitude better than using present equipment.

High sensitivity to atmospheric absorption is a serious limitation of the modified White cell reflectometer. Another limitation is the decrease in signal caused by multiple reflections from mirrors $M_1$, $M_2$, and $M_3$, which may obscure the decreased signal caused by multiple reflections from the sample. Both limitations may be eliminated by using two White cells and making the system double beam. This approach is shown in FIG. 5 with mirrors $M_1$ and $M_3$ mounted on arm 78. Atmospheric path lengths in the sample and reference systems are identical, thus systematic error arising from atmospheric absorption is eliminated by this technique, and errors caused by mirror loss are minimized.

If the mirror to be tested is spherical it and $M_2$ are equivalent to a single fictitious mirror having a different focal length and position. Similarly the sample and $M_1$ or $M_3$ are equivalent to the same single mirror, since $M_s$ is equidistant from $M_2$ and $M_1$ or $M_3$, all of which have the same radius of curvature. Thus to measure a concave spherical mirror $M_1$, $M_2$, and $M_3$ are moved toward the sample by equal distances. For convex mirrors they are moved away from the sample by equal distances. Off axis aberrations which may develop limit this technique, as well as the use of spherical mirrors in these systems, to near normal incidence. Unlike the double reflection beam splitter reflectometer described earlier, the modified White cell reflectometer cannot handle cylindrical optics. It can be used to measure the reflectance of flats over a large range of incident angles.

The reflectometer design using a double reflection from the sample and a spherical mirror is a proven technique for making accurate reflectance measurements and can be used on all types of mirror samples including cylindrical mirrors. The modified White cell reflectometer offers the promise of the increased precision needed to test reflectance values of 0.9995 or better expected in the next generation of mirror coatings now being demonstrated. The major difference between a White cell reflectometer and a double reflection reflectometer is that in the latter the center of curvature of $M_2$ is on the sample surface. In the modified White cell reflectometer, the center of curvature is midway between mirrors $M_1$ and $M_3$. To change the configuration of this reflectometer to that of a White cell system, $M_2$, which is slide mounted, is moved along the bar as shown in FIG. 5 to position 80. S is tilted so that the incident beam strikes $M_1$, and $M_1$ and $M_2$ are adjusted to give the desired number of images on $M_2$. The multiply passed light in a White cell is now detected by a detector 82, which is mounted on the slide 77 holding $M_2$. To make measurements as a function of angle of incidence, $M_1$ and $M_3$, which are slide mounted on a second bar 78 pivoted at P, are rotated along with S. To evaluate spherical mirrors, $M_2$ and $M_1$ are moved equal distances toward or away from S which is equidistant from both. For calibration, S is removed and $M_1$ and $M_3$ are rotated around arc 84 to positions 86 shown in FIG. 5. In position 86, $M_1$, $M_2$ and $M_3$ form a conventional White cell. The signals to detectors 82 and 70 are balanced while in this position by adjusting reference White cell 68. Nearly equal air passage in the two White cells is necessary, but exact equality of signals to detectors 82 and 70 are not required since the function of detector 70 is only to follow detector 82 if source fluctuations occur and to provide a convenient reference signal for ratioing. The same relationship exists between detectors 70 and 72.

A key feature of this reflectometer design is the requirement that the center of curvature of mirror $M_2$ be accurately either on the sample surface or in the surface defined by $M_1$ and $M_3$. For accurate results, the position of $M_2$ should be set to within the focal range of the mirror as in the equation for F given above. Since the instrument is to be a scanning reflectometer, the surface of sample S must rotate and translate in the S plane.

In order for measurements of reflectance and scattered light to be made to the required accuracy over the entire mirror surface, it is necessary to support the mirror to be tested in an unstrained manner and to move either its surface or the test equipment without losing optical registration. The simplest way in which to support a sample S in a vibrationless manner is to use air pads or, if it is to be rotated, to use air bearings and to support it on its back.

Figure 6:
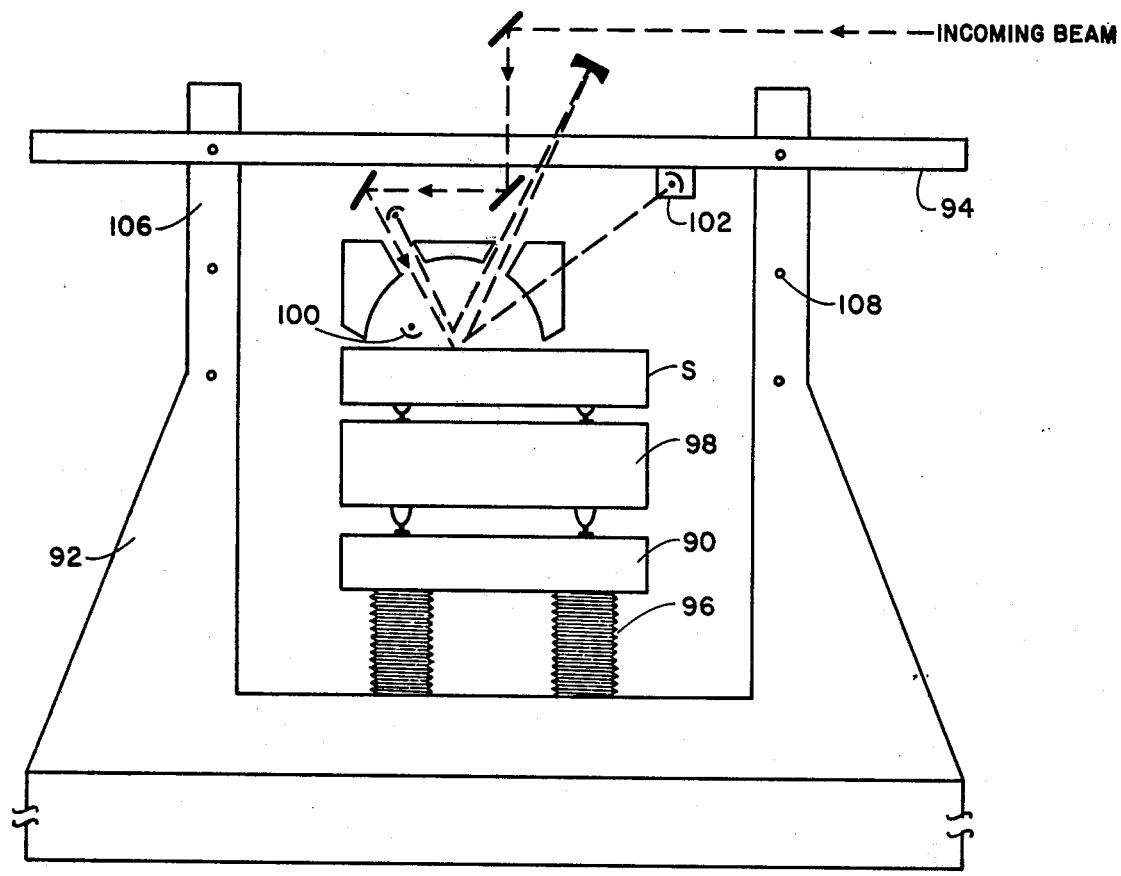
FIG. 6 is a side view of one embodiment of the present invention.

One method of making the measurements as shown in FIG. 5 is the configuration shown in FIG. 6. Desirable tolerances can be achieved using an air bearing rotary table 90 mounted in a concrete and steel weldment 92. Reflectometer optics are mounted on an air bearing track 94. Gross height adjustment is achieved by moving the air bearing slide on weldment 92. Fine adjustment is provided by motor driven jack screws 96. Sample S and the pallet 98 on which it rests are supported kinematically on air bearing rotary table 90. Air bearing tracks 94 also need to be aligned initially but they hold their position thereafter. Checks of the straightness of the track are made by autocollimation on the sample surface. One method for checking that the track is parallel to the mirror surface is to use a Hewett-Packard 5501A doppler interferometer. Other techniques can be devised for this measurement. Although not essential, it is sometimes desirable to measure angular dependence of scattered light as well as total integrated scatter, TIS. TIS is measured by a TIS detector 100. To make a measurement of angular dependence, a detector 102 moves on track 114 at 90° to the main track. By moving this cross track, which is also an air bearing, the entire area above the mirror is measured and the bidirectional reflectance distribution functions, BRDF, for the sample are determined.

Figure 7:
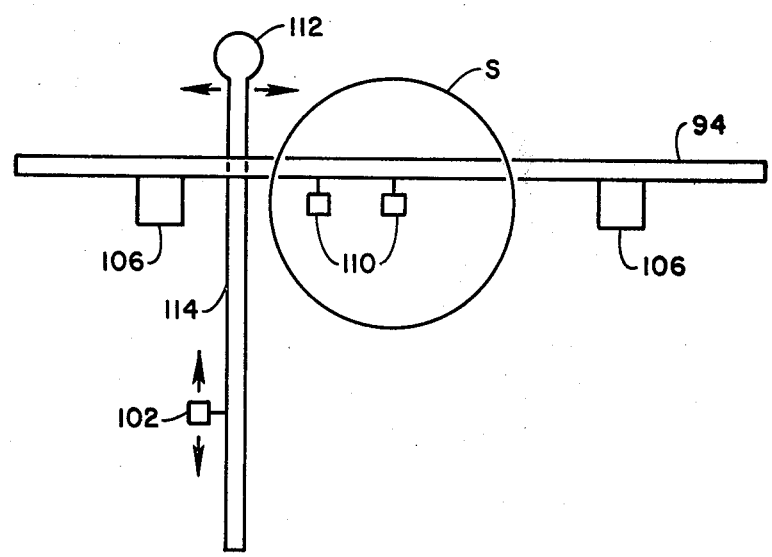
FIG. 7 is a top view of FIG. 6.

A top view of the sample support, showing the cross track, is given in FIG. 7. FIG. 7 is looking down on sample S. Like numbers refer to like components. Vertical supports 106 contain gross height adjusts 108. Beam steering mirrors 110 permit steering of the beam across the entire surface of sample S. To support BRDF detector 102 a slide counterweight 112 is mounted on crossarm 114 to support torque on crossarm 114 due to detector 102.

The advantage of the present system is that one does not need to know the reflectivity of mirrors $M_1$, $M_2$, or $M_3$ or of the reference White cell. Without the sample, it will be determined that one beam is a fixed percentage of the other. For purposes of example, let's assume that in FIG. 5 sample S is removed and mirrors $M_1$ and $M_3$ are placed in position 86 so that the beam intensity in path 66 is 90% of the beam intensity along path 64 through reference White cell as measured by detector 70 and 82. With $M_1$ and $M_3$ rotated back to the position shown in FIG. 5 and mirror $M_2$ moved forward to position 80, numerous reflections occur sufficient to decrease the level of light returning to detector 82 to be 80% of that measured by detector 70. This 10% drop represents an absolute value of loss due to N number of reflections off of the sample surface. Total percent of loss can then be straightforwardly calculated to determine the percentage of reflection on each individual reflection from sample S. If N=50, a loss of 0.2% occurs on each reflection. The reflectivity is determined to be 0.998.

It will be clear to those skilled in the art that numerous modifications of the above principle can be made for a multiple pass absolute reflectometer.

What is claimed is:

1. An absolute reflectometer for a sample mirror or lens comprising:
   a light source emitting a light beam along an optical path;
   a beam splitter placed in said light beam for dividing said light beam into two paths, one of which illuminates said sample about a point;
   a White cell placed in the other of said two paths for establishing a reference level of light intensity;
   a spherical mirror placed so that said mirror's radius of curvature is on the surface of the sample mirror at said point of illumination to reflect light from said beamsplitter via said sample mirror back to said sample mirror and through said beamsplitter;
   a detector placed in the path of light retroreflected through said beamsplitter for measuring the intensity of said retroreflected light; and
   a pivoted arm mounted to said sample mirror for providing a path length for reflection of light when said sample mirror is removed which is equal to the path length when said sample mirror is present.

2. An absolute reflectometer as defined in claim 1 further comprising means for rotating and translating said sample mirror in a given plane, such that measurement of reflection from all sample mirror surface areas can be made.

3. A method of measuring reflection from a sample such as a mirror or lens comprising the steps of:
   (a) emitting light along an optical path;
   (b) dividing said light with a beamsplitter into two separate beams, a sample beam which illuminates said sample, and a reference beam;
   (c) reflecting light from said sample due to said illumination beam back through said beamsplitter along the incoming path via said sample and through said beamsplitter with a spherical mirror such that a virtual image appears;
   (d) placing a White cell in the path of the reference beam to make the path length of the reference beam equal to that of the sample beam;
   (e) measuring the intensity of the reflected light passing through said beamsplitter with a detector;
   (f) establishing the reference level of light through said White cell with a second detector;
   (g) moving said spherical mirror to the virtual image location of said reflected light from said sample; and
   (h) removing said sample so that the sample beam travels a path length equal to the distance travelled prior to the movement of said spherical mirror and the removal of said sample.

4. A method of measuring reflection from a sample as defined in claim 3 further comprising the steps of:
   (i) shifting said sample through a given plane after measuring a given sample surface area in steps (a) through (h); and
   (j) redoing steps (a) through (i) until all of said sample surface area has been measured.

5. A modified White cell for a multiple pass absolute reflectometer to measure a sample object such as a plane mirror, a spherical mirror, or lens, comprising:
   a light source emitting a light beam along an optical path;
   a beamsplitter placed in said optical path to divide said light beam into two separate beams, a sample beam which is incident on said sample, and a reference beam;
   a plurality of mirrors arranged in a White cell configuration to reflect light in the sample beam back and forth for a predetermined number of reflections from said sample object;
   a first detector placed in the path of light from said White cell configuration after it has been reflected off of said sample said predetermined number of times;
   a reference White cell placed in the path of said reference beam for adjusting said reference beam to a predetermined path length;
   a second detector placed after said reference White cell for measuring the amount of light emitted by said reference White cell; and
   a pivoted arm for rotating some of said plurality of mirrors to a position where the light from said beamsplitter is otherwise incident on said sample object travels an equal path length when said sample object is removed, said removal and rotation providing an absolute basis to compare the light lost due to said predetermined number of reflections from said sample.

6. A modified White cell absolute reflectometer as defined in claim 5 further comprising means for rotating and translating said sample in a given plane, such that measurement of reflection from all sample surface areas can be made.

7. A method of measuring the absolute reflection loss from a sample object, such as a mirror or lens, due to multiple reflections from said sample object comprising the steps of:
(a) emitting light along an optical path;
(b) dividing said light with a beamsplitter into two separate beams, a sample beam which is incident on said sample, and a reference beam;
(c) arranging a plurality of mirrors to reflect light in the sample beam back and forth for a predetermined number of reflections from said sample;
(d) placing a detector in the path of said illuminating beam after it has undergone said predetermined number of reflections for measuring the intensity of light present;
(e) removing said sample;
(f) rearranging said plurality of mirrors to form a light path of equal length and with the same number of reflections from said plurality of mirrors, as in step c above but with no reflections from said sample;
(g) mounting a reference White cell in the path of the reference beam to establish a reference level for said light path of said first beam when said sample is removed; and
(h) measuring the light output of said reference White cell with a second detector such that said second detector provides a relative reference level for said first detector capable of adjusting for variations in said light source intensity.

8. The method of claim 7, further comprising the steps of:
(i) shifting said sample in a given plane after measuring a given sample surface area in steps (a) through (h); and
(j) repeating steps a through i until all of said sample surface area has been measured.

* * * * *